(12) United States Patent
Cheng et al.

(10) Patent No.: US 10,928,475 B2
(45) Date of Patent: Feb. 23, 2021

(54) DYNAMIC CONTRAST ENHANCED MAGNETIC RESONANCE IMAGING WITH FLOW ENCODING

(71) Applicant: The Board of Trustees of the Leland Stanford Junior University, Palo Alto, CA (US)

(72) Inventors: Joseph Y. Cheng, Stanford, CA (US); Tao Zhang, Stanford, CA (US); John M. Pauly, Stanford, CA (US); Shreyas S. Vasanawala, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1067 days.

(21) Appl. No.: 14/947,867

(22) Filed: Nov. 20, 2015

(65) Prior Publication Data

US 2017/0146627 A1 May 25, 2017

Related U.S. Application Data

(60) Provisional application No. 62/211,457, filed on Aug. 28, 2015.

(51) Int. Cl.
| | |
|---|---|
| *G01R 33/563* | (2006.01) |
| *A61B 5/055* | (2006.01) |
| *A61B 5/00* | (2006.01) |
| *A61B 5/026* | (2006.01) |
| *G01R 33/56* | (2006.01) |
| *G01R 33/561* | (2006.01) |

(52) U.S. Cl.
CPC ...... *G01R 33/56316* (2013.01); *A61B 5/0263* (2013.01); *A61B 5/055* (2013.01); *A61B 5/7425* (2013.01); *G01R 33/5601* (2013.01); *G01R 33/561* (2013.01)

(58) Field of Classification Search
CPC ................................................ G01R 33/56316
See application file for complete search history.

(56) References Cited

U.S. PATENT DOCUMENTS 7,941,204 B1 * 5/2011 Wang ................. G01R 33/4824
600/420
8,089,278 B1 1/2012 Du
(Continued)

OTHER PUBLICATIONS

Y. Wu et al, Fast Whole-Brain 4D Contrast-Enhanced MR Angiography with Velocity Encoding Using Undersampled Radial Acquisition and Highly Constrained Projection Reconstruction: Image-Quality Assessment in Volunteer Subjects, Mar. 16, 2011, AJNR Am J Neuroradiol, E47-E50, pp. 1-7 (Year: 2011).*
(Continued)

*Primary Examiner* — Rochelle D Turchen
(74) *Attorney, Agent, or Firm* — Beyer Law Group LLP

(57) ABSTRACT

A method for providing magnetic resonance imaging with dynamic contrast and 4D flow of a volume of an object in a magnetic resonance imaging (MRI) system is provided. Contrast agent is provided to the volume of the object. Magnetic resonance excitation from the MRI system is applied to the volume of the object. The MRI system reads out a subsample of less than 10% of spatially resolved data and velocity encoded data with respect to time. The readout subsample is used to determine both dynamic contrast and 4D flow.

18 Claims, 10 Drawing Sheets

(56) References Cited

U.S. PATENT DOCUMENTS

| | | | |
|---|---|---|---|
| 8,890,522 B2 | 11/2014 | Busse | |
| 2010/0286504 A1* | 11/2010 | Mistretta | G01R 33/56509 600/420 |
| 2011/0098556 A1* | 4/2011 | Blomqvist | G01R 33/485 600/419 |
| 2011/0105890 A1* | 5/2011 | Niendorf | G01R 33/4833 600/413 |
| 2014/0210469 A1 | 7/2014 | Cheng et al. | |
| 2014/0236004 A1* | 8/2014 | Rognin | A61B 8/5223 600/431 |
| 2015/0139515 A1* | 5/2015 | Smith | A61B 6/032 382/131 |

OTHER PUBLICATIONS

Saranathan et al., "Differential Subsampling with Cartesian Ordering (DISCO): a high spatio-temporal resolution Dixon imaging sequence for multiphasic contrast enhanced abdominal imaging", J Magn Reson Imaging, 14;35(6); Jun. 2012; pp. 1484-1492. doi:10.1002/jmri.23602 PMID: 22334505, TRIPPS Cheng et al., "Soft-gated accelerated Cartesian 4D flow imaging with intrinsic navigation," 23rd Annual Meeting of ISMRM, 2015, p. 451.

\* cited by examiner

DYNAMIC CONTRAST ENHANCED MAGNETIC RESONANCE IMAGING WITH FLOW ENCODING

CROSS REFERENCE TO RELATED APPLICATIONS

This application claims priority to U.S. Provisional Application No. 62/211,457 filed on Aug. 28, 2015 and entitled "Dynamic-Contrast-Enhanced Magnetic Resonance Imaging with Velocity Encoding" which is hereby incorporated by reference. This invention was made with Government support under contracts EB009690, EB015891, and TR001085 awarded by the National Institutes of Health. The Government has certain rights in the invention.

GOVERNMENT RIGHTS

This invention was made with Government support under contracts P41 EB015891 and R01 EB009690 awarded by the National Institutes of Health. The Government has certain rights in the invention.

BACKGROUND OF THE INVENTION

This invention relates generally to magnetic resonance imaging (MRI). More specifically, the invention relates to dynamic contrast MRI.

Magnetic resonance imaging (MRI) is a non-destructive method for the analysis of materials, and provides medical imaging. It is generally non-invasive and does not involve ionizing radiation. In very general terms, nuclear magnetic moments are excited at specific spin precession frequencies which are proportional to the local magnetic field. The radio-frequency signals resulting from the precession of these spins are received using pickup coils. By manipulating the magnetic fields, an array of signals is provided representing different regions of the volume. These are combined to produce a volumetric image of the nuclear spin density of the body.

MRI is based on nuclear spins, which can be viewed as vectors in a three-dimensional space. During an MRI process, each nuclear spin responds to four different effects: precession about the main magnetic field, nutation about an axis perpendicular to the main field, and both transverse and longitudinal relaxation. In steady-state MRI processes, a combination of these effects occurs periodically.

Compared with other modalities, such as X-ray, CT and ultrasound, MRI takes longer time, sometimes several minutes, for data acquisition to generate clinically useful images. Undesirable imaging artifacts may appear due to the long scan time.

SUMMARY OF THE INVENTION

In accordance with the invention, a method for providing magnetic resonance imaging with dynamic contrast and 4D flow of a volume of an object in a magnetic resonance imaging (MRI) system is provided. Contrast agent is provided to the volume of the object. Magnetic resonance excitation from the MRI system is applied to the volume of the object. The MRI system reads out a subsample of less than 10% of spatially resolved data and velocity encoded data with respect to time. The readout subsample is used to determine both dynamic contrast and 4D flow.

In another manifestation of the invention, a method for providing magnetic resonance imaging with dynamic contrast and 4D flow of a volume of an object in a magnetic resonance imaging (MRI) system is provided. A contrast agent is provided to the volume of the object. Magnetic resonance excitation from the MRI system is applied to the volume of the object. The MRI system reads out a subsample of less than 10% of spatially resolved data and velocity encoded data with respect to time with an accelerated readout. The steps of applying magnetic resonance excitation and reading out a subsample are repeated a plurality of times until the entire volume is readout. The readout out subsample is used to determine both dynamic contrast and 4D flow. Both dynamic contrast and 4D flow are displayed on a display.

In another manifestation of the invention, an apparatus for providing magnetic resonance imaging with dynamic contrast and 4D flow of a volume of an object is provided. A contrast agent system provides a contrast agent to the volume of the object. A magnetic resonance imaging excitation and detection system with a plurality of channels is provided. A controller is electrically connected to the magnetic resonance imaging excitation and detection system. The controller comprises a display, at least one processor, and computer readable media. The computer readable media comprises computer readable code for applying magnetic resonance excitation from the MRI system to the volume of the object, computer readable code for reading out by the MRI system a subsample of less than 10% of spatially resolved data and velocity encoded data with respect to time, computer readable code for using the readout out subsample to determine both dynamic contrast and 4D flow, and computer readable code for displaying both dynamic contrast and 4D flow on the display.

The invention and objects and features thereof will be more readily apparent from the following detailed description and appended claims when taken with the drawings.

DETAILED DESCRIPTION OF ILLUSTRATED EMBODIMENTS

A comprehensive magnetic resonance imaging (MRI) exam with contrast enhancement typically consists of multiple scans to evaluate dynamic contrast enhancement (DCE) characteristics, physiological function, blood flow velocities, and anatomical assessment. For example, standard cardiac MRI protocols consist of separate scans for myocardial perfusion, cardiac function, delayed enhancement, and blood flow quantification.

However, multiple sequences require specially trained MR operators to perform, prolong the exam, and prolong the necessary anesthesia for uncooperative patients, such as pediatric patients. Time-resolved volumetric phase-contrast imaging (4D flow) simplifies the cardiac exams tremendously, especially for congenital heart defect patients. Through a single 4D flow scan that is simple to prescribe, cardiac function, blood flow velocities, and anatomical assessment can be obtained. For more general cardiac protocols, the DCE characterization must also be enabled.

Therefore, some embodiments of the invention are to integrate velocity encoding into a DCE scan for a more comprehensive exam through one MRI sequence. A more integrated sequence further simplifies the acquisition process, makes these types of exams more accessible to sites without specially trained operators, enables more advanced compressed-sensing-based image reconstructions, and enhances post-processing analysis.

Technical Description

Some embodiments can be considered as either (1) a dynamic-contrast-enhanced (DCE) MRI with velocity encoding gradients enabled or (2) a phase-contrast scan with contrast administered during the scan. For generality, some embodiments are described for volumetric imaging with velocity encoding gradients that enables 3-dimensional velocity quantification. However, some embodiments can be applied to 2D phase contrast MRI. An example of the setup of the method is shown in FIG. 1.

Figure 1:
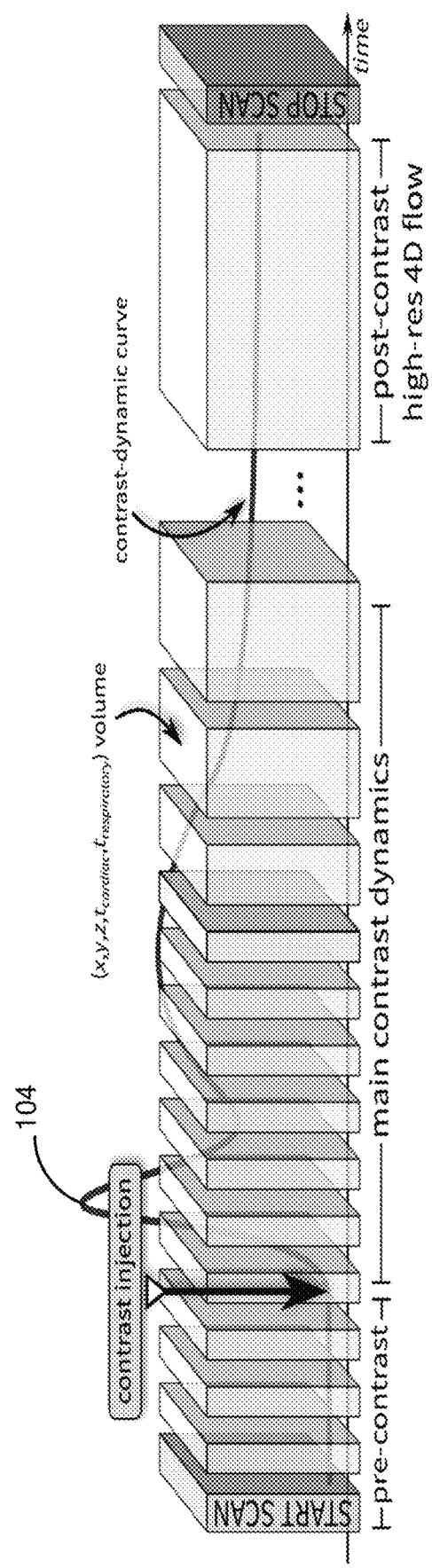
FIG. 1 is a schematic overview of data acquisition.

FIG. 1 is a schematic overview of data acquisition. During the scan, contrast is administered according the a contrast curve 104. The fast hemodynamics is captured with a high temporal resolution. During the post-contrast phases near the end of the scan, the temporal resolution is decreased; this enables a higher quality flow dataset (equivalent to conventional 4D flow imaging). Each volume consists of 3D space with respiratory and cardiac phases.

Method for Data Acquisition

Figure 2A:
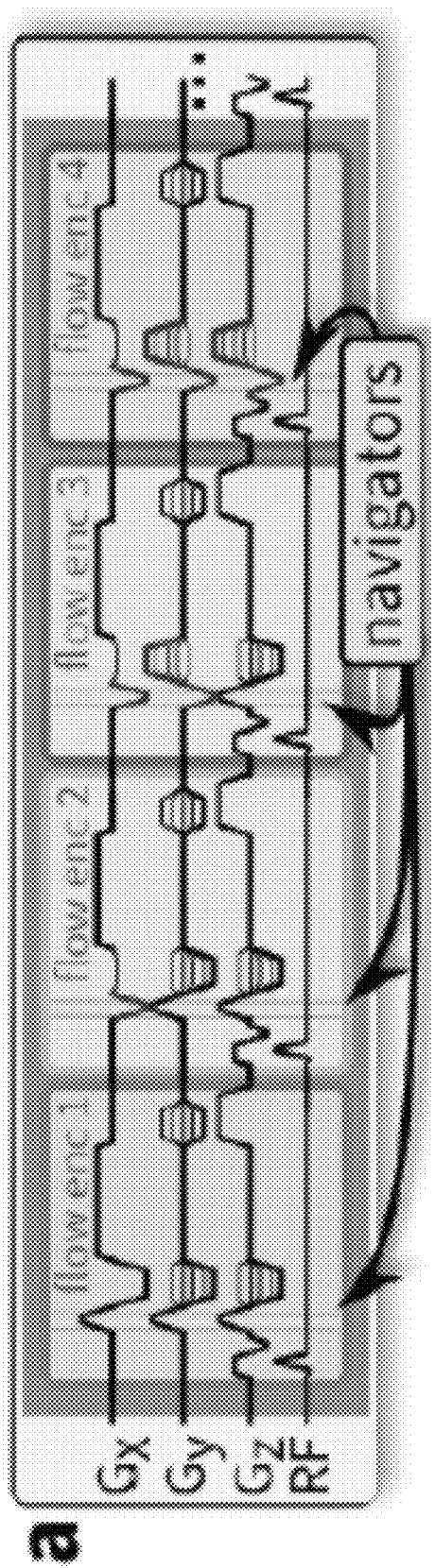
FIGS. 2a-c show an acquisition using Butterfly navigation.
Figure 2B:
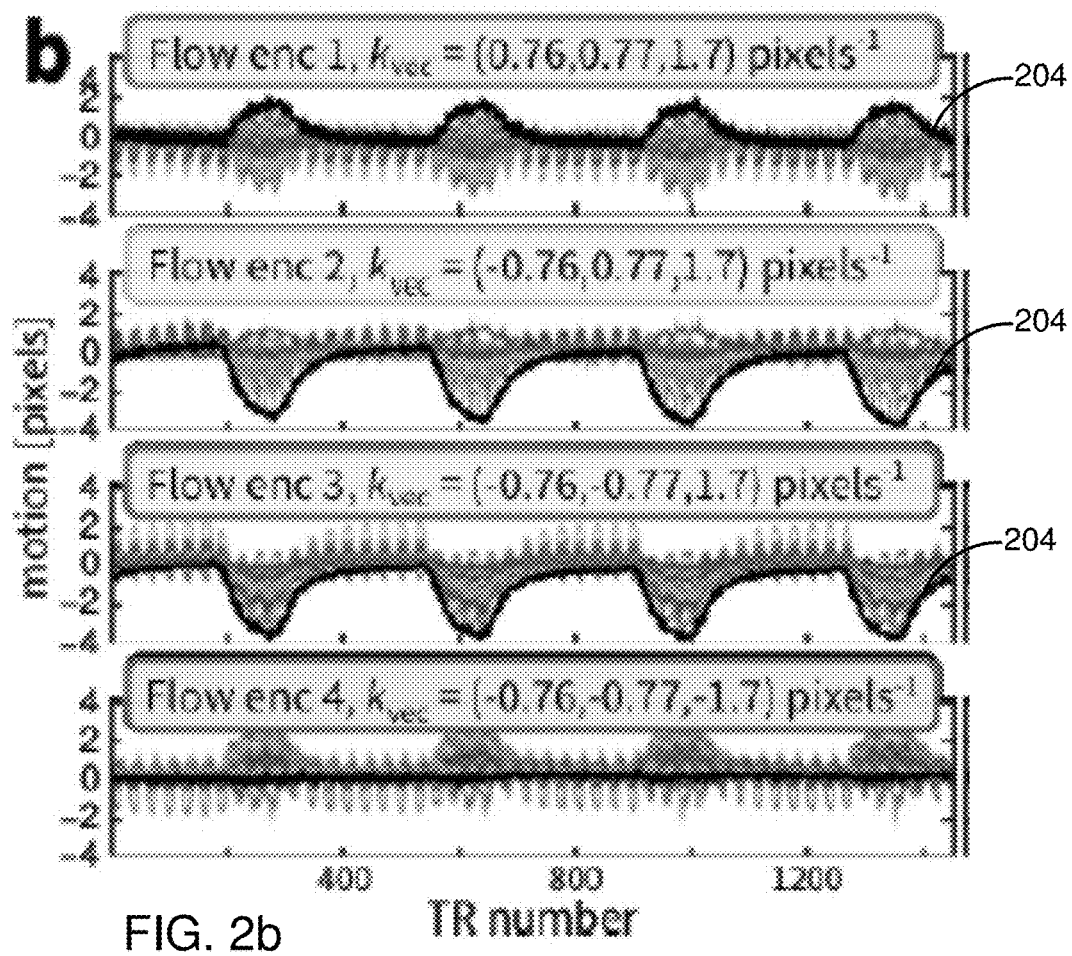
Figure 2C:
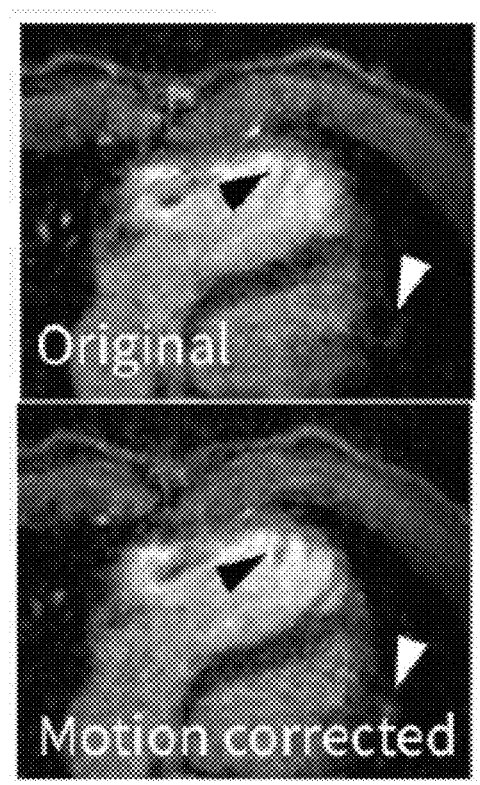

Four velocity-encoding gradient configurations are used to sensitize the acquisition to velocities in four different directions. These four configurations allow for the 3-dimensional velocity to be extracted from the final reconstructions. These velocity-encoding gradients are interleaved throughout the volumetric data acquisition. Not only do these velocity-encoding gradients provide for velocity information, these gradients provide the ability for intrinsic Butterfly navigation as shown in FIGS. 2a-c. Such Butterfly navigation is described in US Patent Publication No. 2014/0210469 A1 by Cheng J Y, Pauly J M, Lustig M, Vasanawala S S and entitled "Nonrigid motion correction in 3D using autofocusing with localized linear translations" and in Cheng J Y, Alley M T, Zhang T, Lai P, Tamir J I, Uecker M, Pauly J M, Lustig M, Vasanawala S S entitled "Soft-gated accelerated Cartesian 4D flow imaging with intrinsic navigation," which are all incorporated by reference for all purposes. The estimated motion is used for determining the respiratory-phase and/or cardiac-phase for each acquired k-space data point.

FIG. 2a illustrates intrinsic navigators built into the velocity-encoding gradients for a phase-contrast sequence. FIG. 2b illustrates example motion waveforms measured from the navigators described in FIG. 2a with the highlighted 204 waveform used to correct the cardiac image of a 22-year-old male, shown in FIG. 2c with a simple rigid-body translation correction to sharpen the cardiac trabecular (black triangle) and vessels (white triangle).

Figures 3A, 3B, 3C:
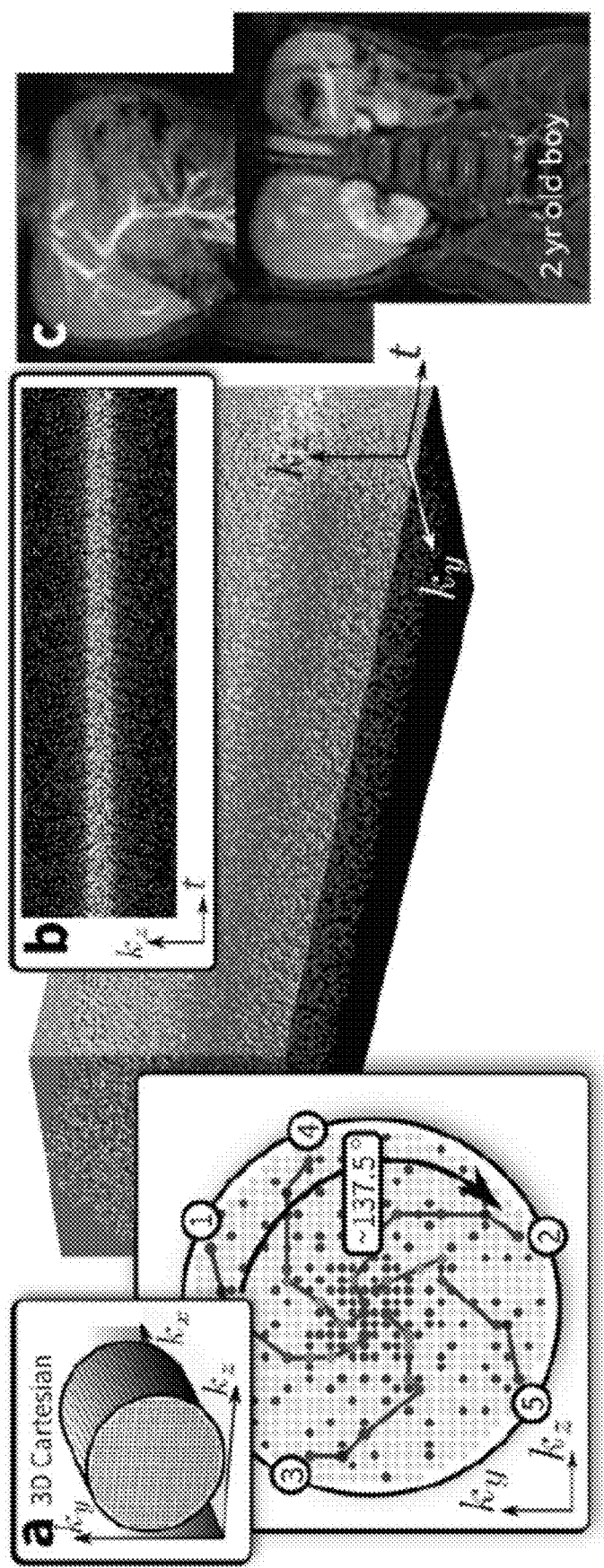
FIGS. 3a-c schematically illustrate a view-ordering and sampling process.

For more ideal sampling in the spatiotemporal space, specially designed sampling schemes should be used. An example is the Variable-Density sampling and Radial view-ordering (VDRad) scheme that groups the Cartesian (ky,kz)-samples into spiral-radial spokes that samples k-space with variable-density (more dense in center k-space and less dense in the outer k-space) as shown in FIGS. 3a-c. These spiral-radial spokes are acquired according to the golden-ratio angle increments for ideal temporal properties. To reduce the time-penalty impact of including 4 different velocity-encoding gradient configurations, the sampling pattern for each of the 4 different velocity-encoding gradient configurations are complementary. In this way, redundant spatial information can be more easily exploited in a keyhole type reconstruction or in a more advanced compressed-sensing-based reconstruction. Depending on the application, the VDRad design can be adapted to produce complementary sampling patterns in the temporal dimension or among the different cardiac-phases. These design considerations enable more ideal setup for compressed-sensing reconstruction that exploits data redundancies in those dimensions.

FIG. 3a shows a variable-density sampling and radial view-ordering (VDRad) approach for 3D Cartesian imaging. FIG. 3b shows the resulting sampling mask using VDRad that is random in both (ky,kz)-space and in time (t). FIG. 3c is images of a free-breathing scan of a 2-year-old boy demonstrating the motion robustness of the scheme.

At a minimum, the VDRad design is constructed for ideal sampling patterns in the temporal dimension. The scan is prescribed to be 5-15 min. The scan is prescribed, started, and the following steps are performed.

1. After approximately 1-2 min, contrast is intravenously administered.

2. The scan continues to run to capture the contrast dynamic characteristics (1-2 min).

3. Afterwards, the scan continues for another 3-11 min for a high-resolution reconstruction.

The first data acquisition portion is used as a baseline for perfusion or DCE analysis. The second portion is to enable a reconstruction that properly characterizes the contrast dynamics. During the last portion, the administered contrast stabilizes and provides high signal-to-noise ratio (SNR) to depict high-resolution anatomical, functional, and flow evaluation. Depending on the desired resolution, this last scan portion can be lengthened or shortened.

Method for Image Reconstruction

The acquisition of this integrated approach is longer than conventional approaches of DCE-only scan or 4D-flow-only scan. A major advantage of this approach is that overall the MR exam duration can be shortened with higher accelerations through compressed-sensing. The integrated scan readily enables an advanced compressed-sensing reconstruction without the need of data synchronization or image registration. The dataset can be reconstructed by solving the following optimization problem:

$$\mathrm{argmin}_m 1/2\|W(Am-y)\|2/2+\lambda_x\|R_x(m)\|_1+\lambda_e\|R_e(m)\|_1+\lambda_t\|R_t(m)\|_1+\lambda_c\|R_c(m)\|_1+\lambda_r\|R_r(m)\|_1. \quad (1)$$

Matrix m is the desired high-dimensional dataset to be reconstructed and y is the acquired k-space data. Matrix A describes the data acquisition model: ESPIRiT-based sensitivity maps, Fourier transform operator, and subsampling operation. Diagonal matrix W is used to weight the data consistency based on known sources of data corruption such as motion for soft-gating. The additional regularization terms, $\lambda_i$ and $R_i(m)$, are used to constrain the reconstruction for compressed sensing. In Eq. (1), separate regularization terms are used to exploit data sparsity in each of the dimensions:

$R_x(m)$ for spatial sparsity such as with a Wavelet operator, $R_e(m)$ for data redundancies among the flow-encoded echoes such as with divergence-free Wavelets, $R_t(m)$ for temporal sparsity among the temporal phases such as with a low-rank operator, $R_c(m)$ for data redundancies among the different cardiac phases such as with a finite-difference operator, and $R_r(m)$ for data redundancies among the different respiratory phases such as with a finite-difference operator.

Depending on the application, different regularization terms can be omitted or included. Furthermore, sparse models that span multiple dimensions can be used such as low-rank as a spatiotemporal property for DCE imaging or low-rank for tensor completion. An example reconstruction using spatial Wavelets and finite differences in the temporal and cardiac dimension is shown in FIGS. 4a-c.

Figure 4A:
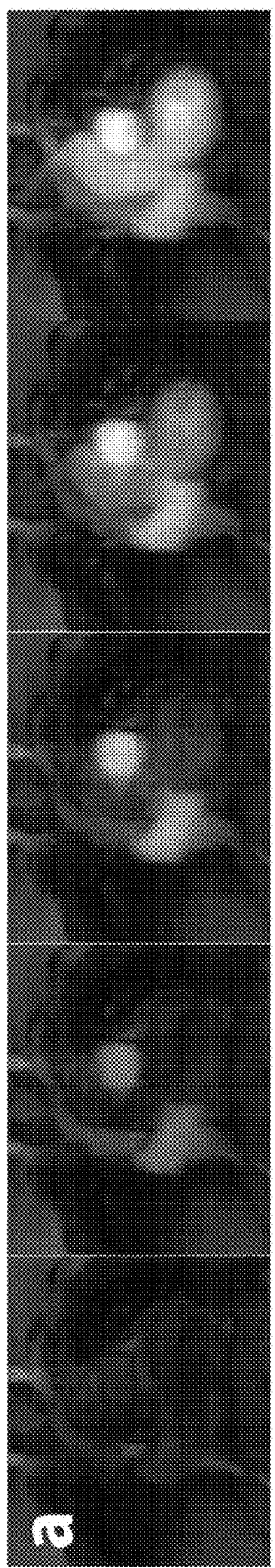
FIGS. 4a-c the feasibility of resolving dynamics and flow in one scan.
Figure 4B:
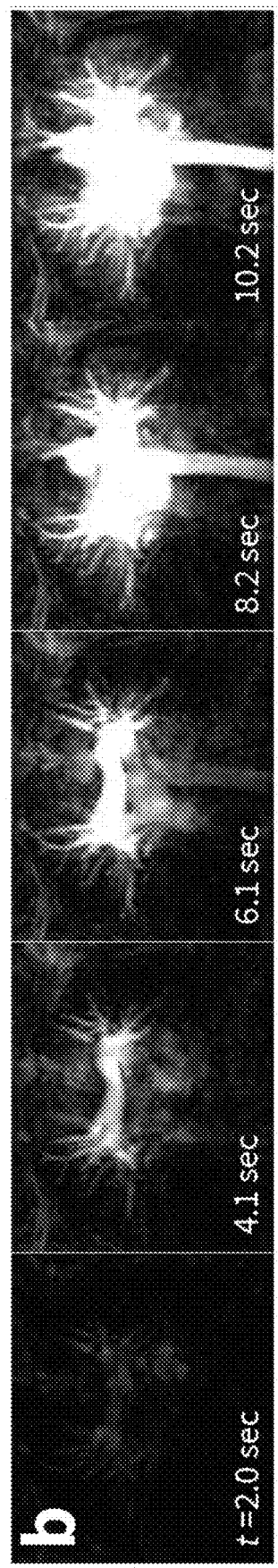
Figure 4C:
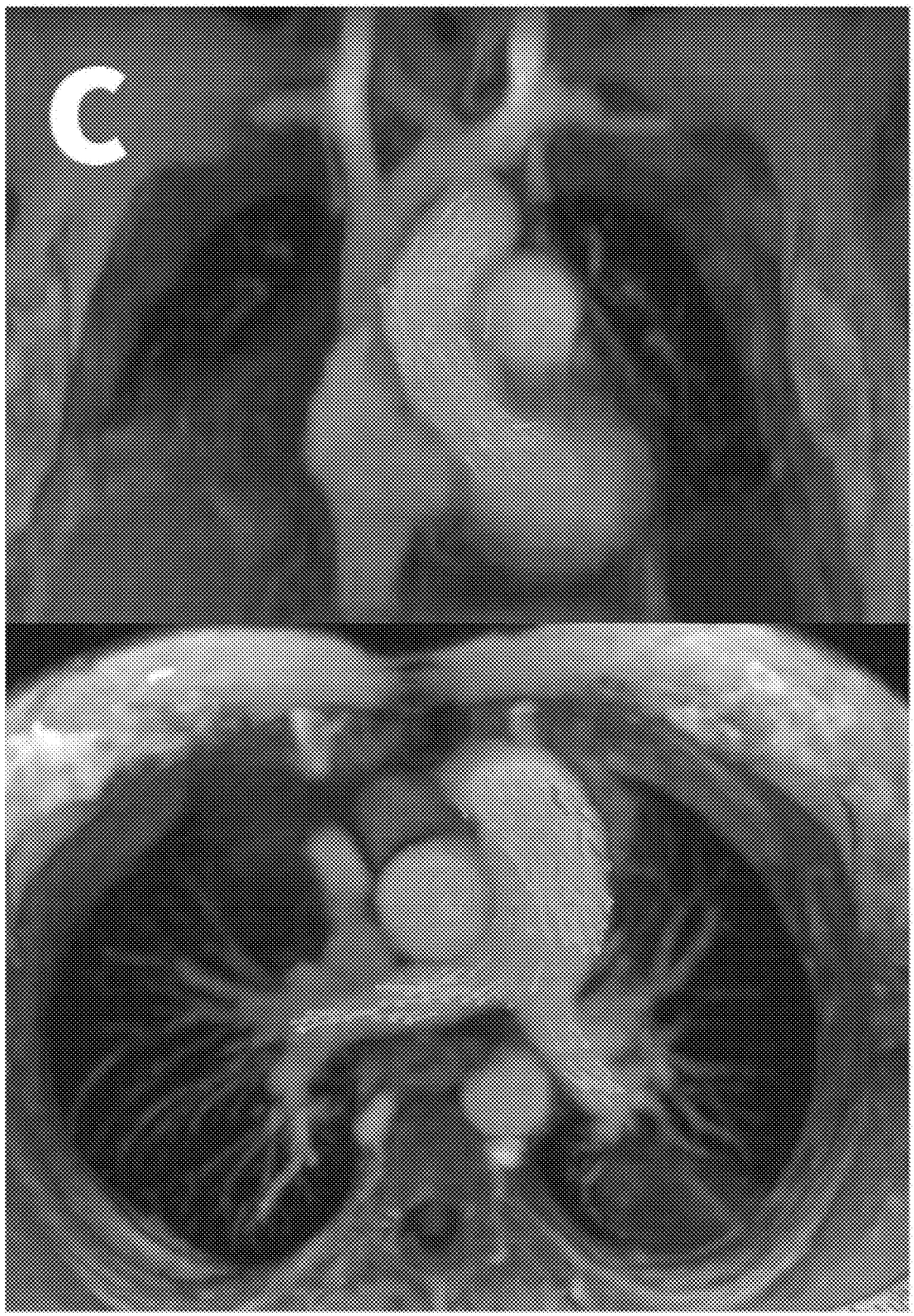

The feasibility of resolving dynamics and flow in one scan is demonstrated in a 24-yr-old female patient with gadolinium-contrast administration, as shown in FIGS. 4a-c. FIG. 4a shows angiography highlighting cardiac function with a 2.1-sec temporal resolution. FIG. 4b shows a similar reconstruction as FIG. 4a, but subtracted each phase with the baseline temporal phase and adjusted window/level to highlight pulmonary perfusion. FIG. 4c shows cardiac-resolved volumetric imaging with blood flow information depicted with velocity vector rendering showing aortic flow (top) and pulmonary flow (bottom). In FIG. 4B, the pulmonary vessels are enhanced first at 4.1 and 6.1 sec. The lungs begin to enhance around 8.2 sec. High-spatial resolution is sacrificed for high-temporal resolution. An embodiment maintains high spatiotemporal resolution to allow for visualization of the different dynamics.

Enhancement to Image Post-Processing Analysis

A major contribution of this invention is the ability to exploit added information for the image post-processing. The DCE and flow information are inherently registered because all such information is acquired from one data acquisition sequence. Two examples are given.

First, for the data processing of cardiac 4D flow information (blood flow velocities, cardiac motion and function, and anatomy), the DCE phases can be used to better highlight either the arteries or veins. The different timing of enhancement of different tissues can be used as an input to determine which features to highlight or omit. An example is shown in FIGS. 5a-c.

Figure 5A:
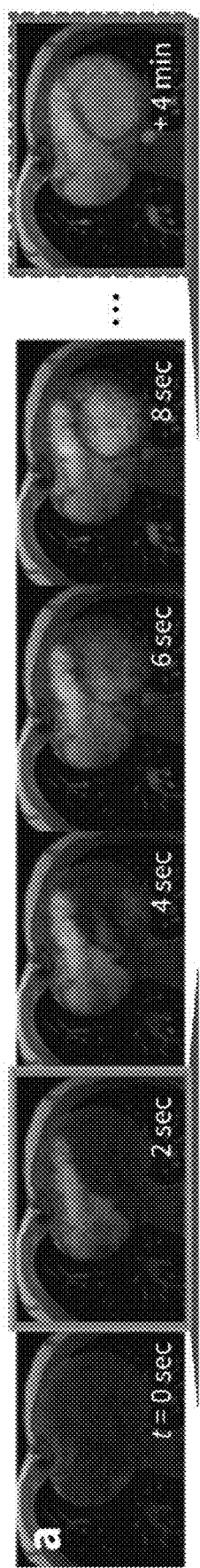
FIGS. 5a-c illustrate an image analysis of myocardial perfusion with 4D flow.
Figure 5C:
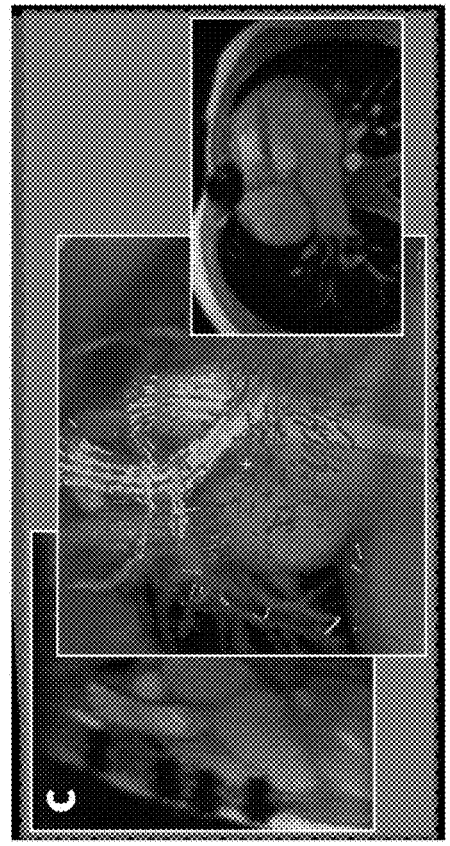
Figure 5B:

FIGS. 5a-c show a myocardial perfusion (gadolinium enhancement) with 4D flow of a 6-yr-old female with left ventricular non-compaction. FIG. 5a shows the myocardial volumetric perfusion is resolved with a temporal rate of 2 sec. FIG. 5b shows that the visualization of the cardiac-phase-resolved volumetric flow data is enhanced with the perfusion data emphasizing the flow in the main pulmonary artery and the superior and inferior vena cava. FIG. 5c shows the same flow information displayed during the post-contrast phases where there is more difficulty in separating flow information from different arteries and vessels. In an embodiment, the additional information from the multi-dimensional dataset may be integrated to enhance visualization as shown in FIG. 5b.

Second, for the data processing of the DCE dataset, blood velocities can be used for more accurate pharmacokinetic modeling. For typical analysis of a DCE dataset, a region of interest is segmented and considered the input function. Since the intravenously administered contrast first arrives from the aorta, the aorta is conventionally chosen, highlighted, and considered as the input function. This input function is used to model the enhancement of tissues. The velocity of the blood flow through the aorta and arteries from the 4D flow component should theoretically improve the model.

Figure 6:
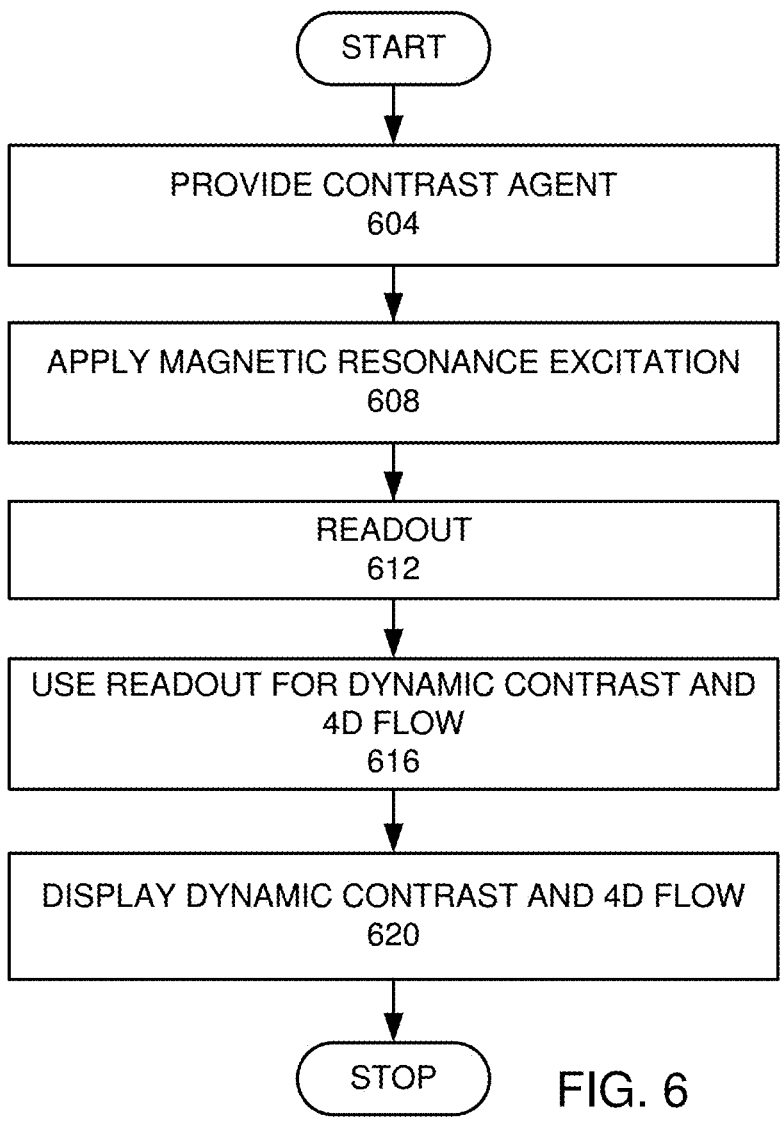
FIG. 6 is a flow chart of an embodiment of the invention.

To facilitate the understanding of the invention, FIG. 6 is a high level flow chart of an embodiment of the invention. A contrast agent is provided to a volume of an object in an MRI system (step 604). An MRI excitation is applied to the volume of the object in the MRI system (step 608). A readout of a subsample of spatial resolved data and velocity encoded data with respect to time is performed (step 612). The readout is able to readout the magnetic field by the MRI system through k-space for a plurality of regions of the object with three spatial dimensions, three velocity dimensions, and a temporal dimension (4D flow readout). The temporal dimension provides dynamic contrast data. In some embodiments, the total data acquisition is subsampled less than 10% of the fully spatially resolved data and velocity encoded data with respect to time. Such a low subsampling percentage increases scanning speed, while providing a sufficiently high resolution. Some embodiments may use several sequences of applying a MRI excitation (step 608) and reading out a volumetric subsample (step 612), where each volumetric readout sequence reads out spatial resolved data and velocity encoded data with respect to time. The readout is used to determine both dynamic contrast and 4D flow (step 616). Dynamic contrast and 4D flow images are displayed (step 620).

Figure 7:
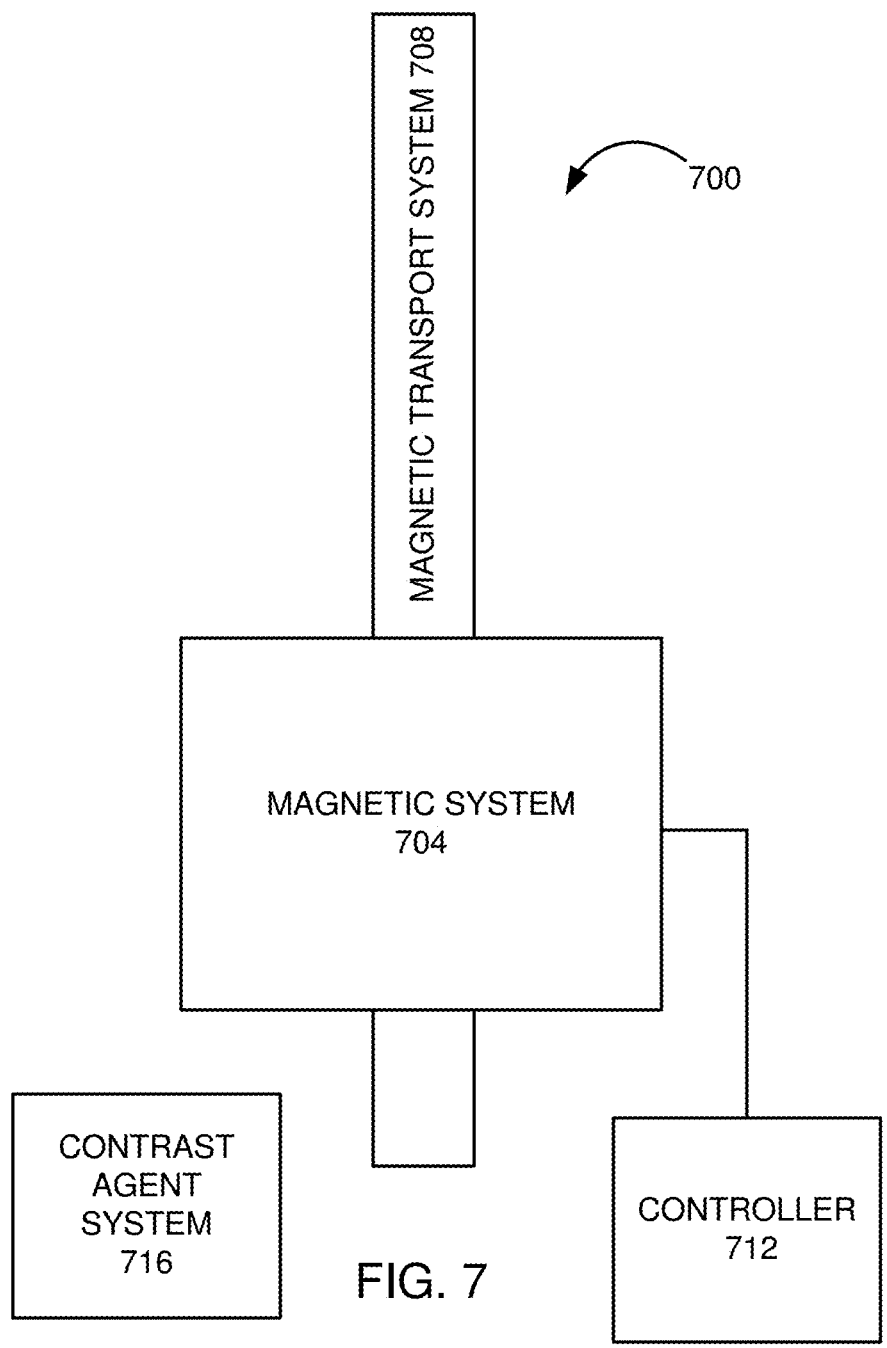
FIG. 7 is a schematic top view of a magnetic resonance imaging (MRI) system that may be used in an embodiment of the invention.

FIG. 7 is a schematic top view of a magnetic resonance imaging (MRI) system 700 that may be used in an embodiment of the invention. The MRI system 700 comprises a magnet system 704, a patient transport table 708 connected to the magnet system, and a controller 712 controllably connected to the magnet system. In one example, a patient would lie on the patient transport table 708 and the magnet system 704 would pass around the patient. The controller 712 would control magnetic fields and radio frequency (RF) signals provided by the magnet system 704 and would receive signals from detectors in the magnet system 704. A contrast agent system 716 provides contrast agent to a body. Such a contrast agent system 716 may comprise a catheter, which provides the contrast agent into the body.

Figure 8:
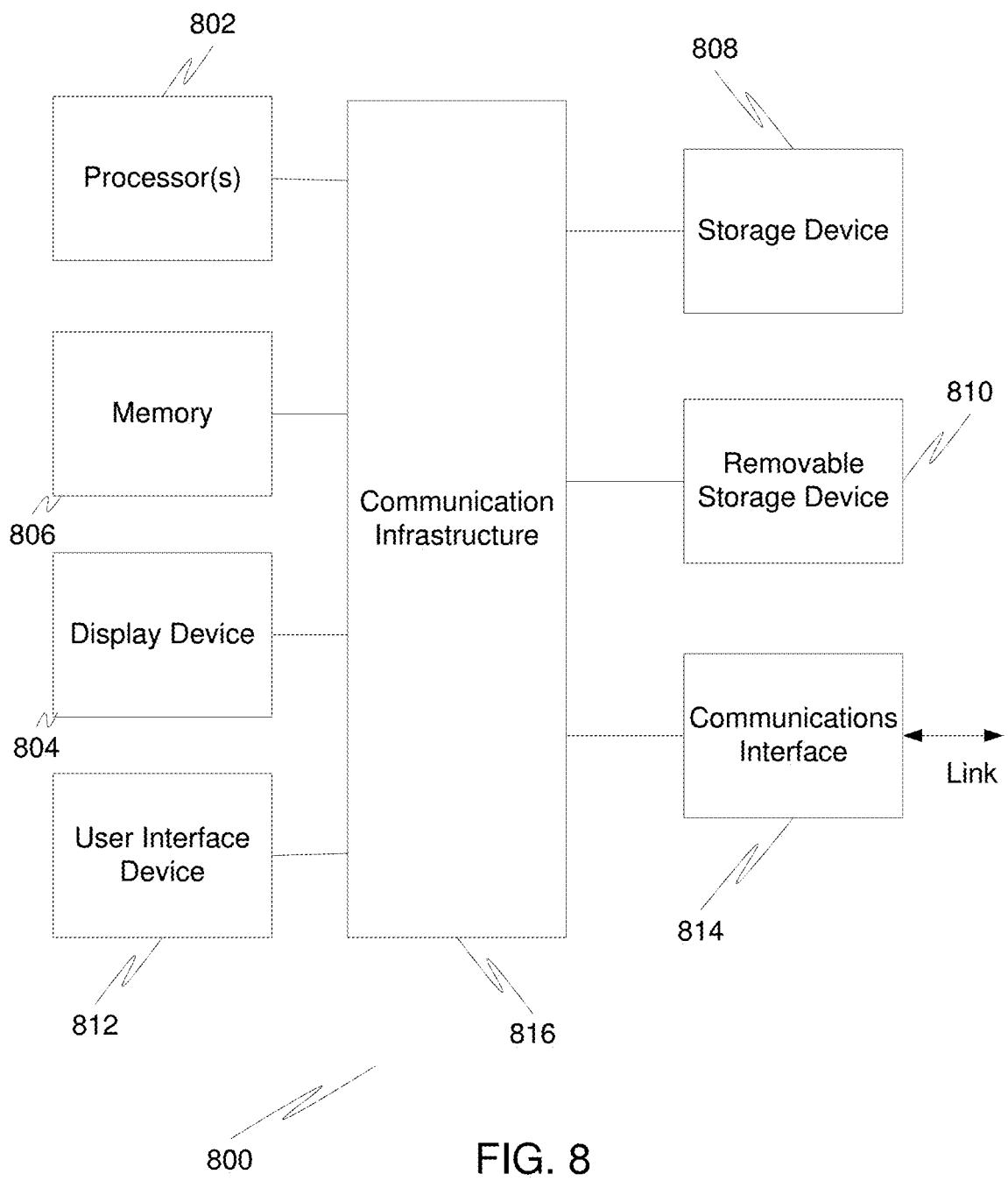
FIG. 8 illustrates a computer system that may be used in an embodiment of the invention.

FIG. 8 is a high level block diagram showing a computer system 800, which may be used to provide the controller 712. The computer system may have many physical forms ranging from an integrated circuit, a printed circuit board, and a small handheld device up to a computer. The computer system 800 includes one or more processors 802, and further can include an electronic display device 804, a main memory 806 (e.g., random access memory (RAM)), storage device 808 (e.g., hard disk drive), removable storage device 810 (e.g., optical disk drive), user interface devices 812 (e.g., keyboards, touch screens, keypads, mice or other pointing devices, etc.), and a communication interface 814 (e.g., wireless network interface). The communication interface 814 allows software and data to be transferred between the computer system 800 and external devices via a link. The system may also include a communications infrastructure 816 (e.g., a communications bus, cross-over bar, or network) to which the aforementioned devices/modules are connected.

Information transferred via communications interface 814 may be in the form of signals such as electronic, electromagnetic, optical, or other signals capable of being received by communications interface 814, via a communication link that carries signals and may be implemented using wire or cable, fiber optics, a phone line, a cellular phone link, a radio frequency link, and/or other communication channels. With such a communications interface, it is contemplated that the one or more processors 802 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

In various embodiments, heart function and/or respiratory function may also be determined from the readout subsample. The heart function and/or respiratory function may also be displayed. Various embodiments may use acceleration to further shorten the data acquisition time. Some embodiments use velocity encoded data to motion correct the spatial resolved data to provide higher spatial resolution from the subsampled data. Advanced reconstruction processes such as keyhole type reconstruction or a more advanced compressed-sensing-based reconstruction may be used for using the readout subsample.

In some embodiments a model of body movement may be created. For example, a model of cardiac or respiratory movement may be created. The readout is fit to the model to accelerate reconstruction. An advantage of an embodiment using a model is that a readout of a scan of the volume may take over a minute, such as several minutes, and yet the time resolution provided may have a resolution of less than a second.

Various embodiments provide different combinations of displays. Some combinations of displays may display dynamic contrast for an arbitrary cardiac phase and respiratory movement. Other combinations of displays may display velocity for a given cardiac phase and respiratory movement. Other embodiments may display cardiac movement, while freezing respiratory movement. Other embodiments may display respiratory movement, while freezing cardiac movement. Other embodiments may display cardiac or respiratory movement with an optimized fixed contrast enhancement.

Various embodiments provide a comprehensive cardiac exam of flow (such as blood flow velocity), anatomy, cardiac function, and contrast enhancement in a single scan and readout sequence. Such a comprehensive cardiac exam provides improved contrast enhancement and cardiac muscle uptake. Such a comprehensive examination is useful in detecting cardiac lesions or scar tissue.

Applications

This invention provides blood flow quantification, functional and anatomical assessment, and contrast enhancement analysis. The invention can be used for cardiac imaging, cardiopulmonary imaging, neuroimaging, oncologic imaging, renal function, and imaging of extremities. This invention can be used in conjunction with any type of MR sampling trajectory. The invention is useful to reduce the total MRI exam duration, which is especially useful to reduce the duration of anesthesia required for imaging uncooperative patients.

Advantages & Improvements

This invention combines the acquisition of the dynamic-contrast-enhancement (DCE) MRI acquisition with the phase-contrast imaging acquisition. This integration provides for a number of advantages and improvements.

With the data acquisition integrated, data redundancies for the DCE dataset and the phase-contrast dataset is easily exploited for higher scan reduction factors in an advanced compressed-sensing-based reconstruction. As a result, the total MRI exam duration is decreased.

The Butterfly navigators from the flow-encoding gradients are automatically used for the DCE dataset reconstruction.

No image registration and warping are necessary to combine the information from the DCE dataset and the phase-contrast dataset. As a result, more advanced post-processing image analysis tools are easily used. For example, a DCE-enhanced 4D flow.

Possible Variations or Modifications

Besides VDRad, other types of Cartesian data acquisition sampling schemes that is pseudo-random in higher-dimensional space can be used. This includes Differential Sub-sampling with Cartesian Ordering (DISCO), which is described in "DIfferential Subsampling with Cartesian Ordering (DISCO): a high spatio-temporal resolution Dixon imaging sequence for multiphasic contrast enhanced abdominal imaging" by Saranathan M, Rettmann D W, Hargreaves B A, Clarke S E, Vasanawala S S, J Magn Reson Imaging, 2012 Jun. 14; 35(6):1484-1492, as described in U.S. Pat. No. 8,089,278, entitled "Time-Resolved Contrast-Enhanced Magnetic Resonance (MR) Angiography," by Du, which issued Jan. 3, 2012, and other pseudo-random schemes, such as described in U.S. Pat. No. 8,890,522, entitled "Accelerated pseudo-random data magnetic resonance imaging system and method," by Busse et al, which issued Nov. 18, 2014, which are all incorporated by reference for all purposes. Additionally, different types of k-space sampling can be used for the data acquisition. This includes non-Cartesian trajectories such as spiral sampling (stack of spirals), radial sampling (3DPR and stack of stars), and cones. Various embodiments can be used for both 2-dimensional and 3-dimensional (in the spatial dimension) techniques. Though the invention relies on compressed-sensing-based reconstruction to enable clinical feasible scan durations, many different regularization terms and models can be used to constrain the reconstruction. The contrast enhancement feature of the invention can be used for perfusion and dynamic-contrast-enhancement analysis, and angiography. The velocity-encoding feature of the invention can be used for quantifying blood flow velocities, tissue movement (such as cardiac motion), and diffusion characteristics.

Various embodiments of the invention combine two types of imaging techniques (phase contrast imaging and dynamic-contrast-enhanced imaging) into one sequence. More specifically, a sequence with flow encoding is used to acquire data during contrast enhancement. This allows for novel advanced reconstruction techniques that can better exploit the data redundancies between the two techniques for enabling higher scan reduction factors and for shortening the duration of the overall MR examination. Furthermore, the combined information about contrast dynamics, flow, function, and anatomy enables novel post-processing techniques to enhance the data analysis.

The invention can be used to obtain images with optimal contrast and/or motion dynamics. Because typical these acquisitions are on the order of 5-15 min, different physiological dynamics may be changing throughout the acquisition: contrast-enhancement changing, heart rate changing, patient bulk movement, and/or respiratory rate changing. It is more accurate to resolve these dynamics rather than attempting to ignore or to correct for them. For example, for optimal contrast-enhanced 4D flow, different temporal windows of 4D flow data can be reconstructed. The more accurate 4D flow reconstruction can be selected for diagnosis.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A method for providing magnetic resonance imaging with dynamic contrast and cardiac-phase-resolved volumetric (4D) flow of a volume of an object in a magnetic resonance imaging (MRI) system, comprising:
    providing contrast agent to the volume of the object;
    applying magnetic resonance excitation from the MRI system to the volume of the object;
    reading out by the MRI system a subsample of less than 10% of spatially resolved data and velocity encoded data with respect to time, wherein the reading out acquires dynamic contrast data and cardiac-phase-resolved volumetric (4D) flow data from one data acquisition sequence; and
    determining both dynamic contrast and cardiac-phase-resolved volumetric (4D) flow by applying both phase contrast image reconstruction and dynamic-contrast-enhanced image reconstruction to the readout subsample, wherein the determining both dynamic contrast and cardiac-phase-resolved volumetric (4D) flow by applying both phase contrast image reconstruction and dynamic-contrast-enhanced image reconstruction to the readout subsample is determined without warping and without image registration.

2. The method, as recited in claim 1, further comprising displaying both dynamic contrast and cardiac-phase-resolved volumetric (4D) flow.

3. The method, as recited in claim 2, further comprising using the readout subsample to determine heart function and respiratory function.

4. The method, as recited in claim 3, further comprising displaying heart and/or respiratory function at a most optimal contrast-enhancement phase.

5. The method, as recited in claim 3, further comprising displaying heart function and respiratory function.

6. The method, as recited in claim 3, further comprising displaying dynamic contrast with respiratory movement for any cardiac phase.

7. The method, as recited in claim 3, further comprising displaying velocity with respiratory movement for any cardiac phase.

8. The method, as recited in claim 3, further comprising displaying respiratory movement with frozen cardiac movement.

9. The method, as recited in claim 3, further comprising displaying cardiac or respiratory movement with an optimized contrast on a display.

10. The method, as recited in claim 3, further comprising displaying cardiac movement for a respiratory state.

11. The method, as recited in claim 1, wherein the reading out by the MRI system a subsample of less than 10% of spatially resolved data and velocity encoded data with respect to time uses Variable-Density sampling and Radial view-ordering (VDRad) scheme that groups the Cartesian (ky,kz)-samples into spiral-radial spokes that samples k-space with variable-density.

12. The method, as recited in claim 1, further comprising using the velocity encoded data to motion correct the spatial resolved data.

13. The method, as recited in claim 1, further comprising using compressed sensing.

14. The method, as recited in claim 1, wherein the determining both dynamic contrast and cardiac-phase-resolved volumetric flow (4D) fits the subsample to a model using a function of cardiac and respiratory movement.

15. The method, as recited in claim 1, wherein the applying the magnetic resonance from the MRI system to the volume of the object and reading out a subsample of less than 10% of spatial resolved data and velocity encoded data with respect to time takes over a minute to readout the entire volume once, and wherein a time resolution of less than one second is provided.

16. A method for providing magnetic resonance imaging with dynamic contrast and cardiac-phase-resolved volumetric (4D) flow of a volume of an object in a magnetic resonance imaging (MRI) system, comprising:
    a) providing contrast agent to the volume of the object;
    b) applying magnetic resonance excitation from the MRI system to the volume of the object;
    c) reading out by the MRI system a subsample of less than 10% of spatially resolved data and velocity encoded data with respect to time with an accelerated readout, wherein the reading out acquires dynamic contrast data and cardiac-phase-resolved volumetric (4D) flow data from one data acquisition sequence;
    d) repeating steps b and c a plurality of times until the entire volume is readout;
    e) using the readout subsample to determine both dynamic contrast and cardiac-phase-resolved volumetric (4D) flow, by applying both phase contrast image reconstruction and dynamic-contrast-enhanced image reconstruction to the readout subsample, wherein the determining both dynamic contrast and cardiac-phase-resolved volumetric (4D) flow by applying both phase contrast image reconstruction and dynamic-contrast-enhanced image reconstruction to the readout subsample is determined without warping and without image registration; and
    displaying both dynamic contrast and cardiac-phase-resolved volumetric (4D) flow on a display.

17. An apparatus for providing magnetic resonance imaging with dynamic contrast and cardiac-phase-resolved volumetric (4D) flow of a volume of an object, comprising:
    a magnetic resonance imaging excitation and detection system; and
    a controller electrically connected to the magnetic resonance imaging excitation and detection system, comprising:
        a display;
        at least one processor; and
        computer readable media, comprising:

computer readable code for applying magnetic resonance excitation from the MRI system to the volume of the object;

computer readable code for reading out by the MRI system a subsample of less than 10% of spatially resolved data and velocity encoded data with respect to time, wherein the reading out acquires dynamic contrast data and cardiac-phase-resolved volumetric (4D) flow data from one data acquisition sequence;

computer readable code for using the readout subsample to determine both dynamic contrast and cardiac-phase-resolved volumetric 4D by applying both phase contrast image reconstruction and dynamic-contrast-enhanced image reconstruction to the readout subsample, wherein the determining both dynamic contrast and cardiac-phase-resolved volumetric (4D) flow by applying both phase contrast image reconstruction and dynamic-contrast-enhanced image reconstruction to the readout subsample is determined without warping and without image registration; and computer readable code for displaying both dynamic contrast and cardiac-phase-resolved volumetric (4D) flow on the display.

18. The method, as recited in claim 1, wherein the reading out by the MRI system a subsample of less than 10% of spatially resolved data and velocity encoded data with respect to time is an integrated phase contrast imaging and dynamic-contrast-enhanced imaging data acquisition.

* * * * *